United States Patent
Rajan et al.

(10) Patent No.: US 10,734,101 B2
(45) Date of Patent: Aug. 4, 2020

(54) METHOD AND SYSTEM TO PROCESS ELECTRONIC MEDICAL RECORDS FOR PREDICTING HEALTH CONDITIONS OF PATIENTS

(71) Applicant: Conduent Business Services, LLC, Dallas, TX (US)

(72) Inventors: Vaibhav Rajan, Bangalore (IN); Vijay Huddar, Bijapur (IN)

(73) Assignee: Conduent Business Services, LLC, Florham Park, NJ (US)

( * ) Notice: Subject to any disclaimer, the term of this patent is extended or adjusted under 35 U.S.C. 154(b) by 764 days.

(21) Appl. No.: 15/205,058

(22) Filed: Jul. 8, 2016

(65) Prior Publication Data

US 2018/0011972 A1    Jan. 11, 2018

(51) Int. Cl.
| | | |
|---|---|---|
| *G16H 10/60* | (2018.01) | |
| *G16H 50/30* | (2018.01) | |
| *G06F 16/93* | (2019.01) | |
| *G06F 16/95* | (2019.01) | |
| *G06F 16/28* | (2019.01) | |
| *G06F 16/901* | (2019.01) | |
| *G06F 16/2457* | (2019.01) | |

(Continued)

(52) U.S. Cl.
CPC ....... *G16H 10/60* (2018.01); *G06F 16/24578* (2019.01); *G06F 16/285* (2019.01); *G06F 16/9024* (2019.01); *G06F 16/93* (2019.01); *G06F 16/95* (2019.01); *G06F 40/30* (2020.01); *G16H 50/20* (2018.01); *G16H 50/30* (2018.01); *G16H 50/70* (2018.01)

(58) Field of Classification Search
CPC ...................................................... G16H 10/60
See application file for complete search history.

(56) References Cited

U.S. PATENT DOCUMENTS 8,195,693 B2 * 6/2012 Syeda-Mahmood ... G06F 16/25
707/790
9,189,855 B2 * 11/2015 Guigues ................. G06T 7/246
(Continued)

OTHER PUBLICATIONS

Vivi Nastase, Rada Mihalcea, and Dragomir R. Radev. "A survey of graphs in natural language processing." Natural Language Engineering 21 (5): pp. 665-697. Cambridge University Press. (Year: 2015).*

(Continued)

*Primary Examiner* — Robert A Sorey
*Assistant Examiner* — Kristine K Rapillo
(74) *Attorney, Agent, or Firm* — Jones Robb, PLLC

(57) ABSTRACT

A method and a system are provided for processing electronic medical records for predicting a health condition of a patient. The method may determine a first set of datasets of a first patient based on one or more first electronic medical records. The method may extract one or more second sets of datasets of one or more second patients from a database server based on the first set of datasets. The method may generate one or more bipartite graphs based on the first set of datasets and the one or more second sets of datasets. The method may determine a set of edges from the one or more edges based on a matching score in each bipartite graph. The method may further predict the health condition of the first patient based on at least the matching score associated with each of the one or more bipartite graphs.

20 Claims, 5 Drawing Sheets

(51) Int. Cl.
*G16H 50/20* (2018.01)
*G16H 50/70* (2018.01)
*G06F 40/30* (2020.01)

(56) References Cited

U.S. PATENT DOCUMENTS

| | | | | |
|---|---|---|---|---|
| 2013/0231953 | A1* | 9/2013 | Ebadollahi | G06Q 50/22 705/3 |
| 2013/0311201 | A1* | 11/2013 | Chatfield | G16H 50/20 705/3 |
| 2017/0032273 | A1* | 2/2017 | Ho | G06N 20/00 |

OTHER PUBLICATIONS

Vivi Nastase, Rada Mihalcea, and Dragomir R. Radev. "A survey of graphs in natural language processing." Natural Language Engineering 21 (5): pp. 665-697. Cambridge University Press 2015 (Year: 2015).*

Martin Ester, Hans-Peter Kriegel, Jorg Sander, and Xiaowei Xu. A density-based algorithm for discovering clusters in large spatial databases with noise. In KDD, vol. 96, pp. 226-231, 1996.

Marzyeh Ghassemi, Marco AF Pimentel, Tristan Naumann, Thomas Brennan, David A Clifton, Peter Szolovits, and Mengling Feng. A multivariate timeseries modeling approach to severity of illness assessment and forecasting in ICU with sparse, heterogeneous clinical data. In AAAI, 2015.

Genevieve B Melton and George Hripcsak. Automated detection of adverse events using natural language processing of discharge summaries. Journal of the American Medical Informatics Association, 12(4):448{457, 2005.

Leonard Kaufman and Peter Rousseeuw. Clustering by means of medoids. North-Holland, 1987.

Christian B ohm, Claudia Plant, Junming Shao, and Qinli Yang. Clustering by synchronization. In Proceedings of the 16th ACM SIGKDD international conference on Knowledge discovery and data mining, pp. 583-592. ACM, 2010.

Budhaditya Saha, Duc-Son Pham, Dinh Phung, and Svetha Venkatesh. Clustering patient medical records via sparse subspace representation. In Advances in Knowledge Discovery and Data Mining, vol. 7819 of Lecture Notes in Computer Science, pp. 123-134. 2013.

Anthony KH Tung, Xin Xu, and Beng Chin Ooi. Curler:finding and visualizing nonlinear correlation clusters. In Proceedings of the 2005 ACM SIGMOD international conference on Management of data, pp. 467-478. ACM, 2005.

Anil K Jain. Data clustering: 50 years beyond k-means. Pattern Recognition Letters, 31(8):651-666, 2010.

Francis R Bach and Michael I Jordan. Learning spectral clustering. In NIPS, vol. 16, 2003.

Stuart Lloyd. Least squares quantization in PCM. Information Theory, IEEE Transactions on, 28(2):129{137, 1982.

A. P. Dempster, N. M. Laird, and D. B. Rubin. Maximum likelihood from incomplete data via the EM algorithm. Journal of the Royal Statistical Society, Series B, 39(1):1{38, 1977.

Kamalika Chaudhuri, Sham M Kakade, Karen Livescu, and Karthik Sridharan. Multi-view clustering via canonical correlation analysis. In Proceedings of the 26th annual international conference on machine learning, pp. 129-136. ACM, 2009.

Mihael Ankerst, Markus M Breunig, Hans-Peter Kriegel, and J org Sander. Optics: ordering points to identify the clustering structure. In ACM Sigmod Record, vol. 28, pp. 49-60. ACM, 1999.

Marzyeh Ghassemi, Tristan Naumann, Finale Doshi-Velez, Nicole Brimmer, Rohit Joshi, Anna Rumshisky, and Peter Szolovits. Unfolding physiological state: mortality modelling in intensive care units. In Proceedings of the 20th ACM SIGKDD international conference on Knowledge discovery and data mining, pp. 75-84. ACM, 2014.

A. L. Goldberger, L. A. N. Amaral, L. Glass, J. M. Hausdor_, P. Ch. Ivanov, R. G. Mark, J. E. Mietus, G. B. Moody, C.-K. Peng, and H. E. Stanley. PhysioBank, PhysioToolkit, and PhysioNet: Components of a new research resource for complex physiologic signals. Circulation, 101(23):e215{e220, (Jun. 13, 2000).

* cited by examiner

METHOD AND SYSTEM TO PROCESS ELECTRONIC MEDICAL RECORDS FOR PREDICTING HEALTH CONDITIONS OF PATIENTS

TECHNICAL FIELD

The presently disclosed embodiments are related, in general, to healthcare systems. More particularly, the presently disclosed embodiments are related to a method and system of processing electronic medical records for predicting a health condition of a patient.

BACKGROUND

Currently, data driven approaches are extensively used in several domains, such as finance, healthcare, life sciences, and social and physical sciences, for discovering data patterns. Unsupervised learning methods, such as clustering or self-organizing maps, are the most preferred tools for discovering data patterns.

In the field of healthcare analytics, clustering is extensively used to discover patterns in disease risk profiles and treatment responses based on common procedures, such as stratification of patients. Such procedures may be used at various levels, such as for analyses within a hospital, using electronic medical records or electronic health records and population-level analyses in hospital information systems (HIS). A clustering method, such as partitioning-based clustering (such as K-Means), relies on a measure of similarity or distance between at least two objects being clustered. The efficacy of such methods depends on a distance metric used, such as Euclidean distance, cosine similarity, and Jaccard distance, which in turn depends on the data and the application. While such distance metrics are useful in a large number of applications, other applications may require the use of specialized distance metrics.

In healthcare analytics, patient data that includes unstructured notes, such as discharge summaries and nursing notes, are clustered by using text-processing techniques. The text in the unstructured notes may be analyzed to determine several postoperative complications, detect clinical conditions in an ailment with a consistency that is indistinguishable from that of physicians reviewing the same reports, and predict mortality in the intensive care units (ICUs). In certain scenarios, based on the vast amount of real-time information associated with different health-related parameters of a patient, it may be difficult to predict certain medical conditions that may need immediate attention. Thus, an automated technique may be desired to cluster the recorded medical reports of a patient in a structured manner for predicting the health of the patient.

Further limitations and disadvantages of conventional and traditional approaches will become apparent to a person having ordinary skill in the art, through comparison of described systems with some aspects of the present disclosure, as set forth in the remainder of the present application and with reference to the drawings.

SUMMARY

According to embodiments illustrated herein, there may be provided a method to process electronic medical records to predict a health condition of a first patient. The method may comprise determining, by a document processor, a first set of datasets of a first patient based on one or more first electronic medical records, associated with the first patient, received from a computing device over a communication network. The method further comprise extracting, by a processor at the server, one or more second sets of datasets of one or more second patients from a database server based on at least the first set of datasets of the first patient. The method further comprise generating, by a graphical processor at the server, one or more bipartite graphs based on the first set of datasets and the one or more second sets of datasets, wherein a bipartite graph includes one or more edges with corresponding weights between each of the first set of datasets and each of the one or more second sets of datasets. The method may further comprise determining, by a natural language processor at the server, a set of edges from the one or more edges based on a weight associated with each of the one or more edges. The method may further comprise determining, by the processor, a matching score based on at least a count of edges in the set of edges and a weight associated with each of the set of edges. The method further includes predicting, by the natural language processor, the health condition of the first patient based on at least the matching score associated with each of the one or more bipartite graphs.

According to embodiments illustrated herein, there may be provided a system for processing electronic medical records for predicting a health condition of a patient. The system may comprise a document processor in a server that are configured to determine a first set of datasets of a first patient based on one or more first electronic medical records, associated with the first patient, received from a computing device over a communication network. The system may further comprise a processor in the server that may be configured to extract one or more second sets of datasets of one or more second patients from a database server based on at least the first set of datasets of the first patient. The system may further comprise a graphical processor in the server that may be configured to generate one or more bipartite graphs based on the first set of datasets and the one or more second sets of datasets, wherein a bipartite graph includes one or more edges with corresponding weights between each of the first set of datasets and each of the one or more second sets of datasets. The system may further comprise a natural language processor in a server that may be configured to determine a set of edges from the one or more edges based on a weight associated with each of the one or more edges. The processor in a server may further be configured to determine a matching score based on at least a count of edges in the set of edges and a weight associated with each of the set of edges. The system may further comprise a natural language processor in a server that may be configured to predict the health condition of the first patient based on at least the matching score associated with each of the one or more bipartite graphs.

According to embodiments illustrated herein, there is provided a computer program product for use with a computing device. The computer program product comprises a non-transitory computer readable medium storing a computer program code for processing electronic medical records for predicting a health condition of a patient. The computer program code is further executable by a document processor to determine a first set of datasets of a first patient based on one or more first electronic medical records. The computer program code is further executable by a processor to extract one or more second sets of datasets of one or more second patients from a database server based on at least the first set of datasets of the first patient. The computer program code is executable by a graphical processor to generate one or more bipartite graphs based on the first set of datasets and the one or more second sets of datasets, wherein a bipartite graph includes one or more edges with corresponding weights between each of the first set of datasets and each of the one or more second sets of datasets. The computer program code is executable by a natural language processor to determine a set of edges from the one or more edges based on a weight associated with each of the one or more edges. Further, the computer program code is executable to determine, by the processor, a matching score based on at least a count of edges in the set of edges and a weight associated with each of the set of edges. Further, the computer program code is executable by a natural language processor to predict the health condition of the first patient based on at least the matching score associated with each of the one or more bipartite graphs.

BRIEF DESCRIPTION OF DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not to limit the scope in any manner, wherein like designations denote similar elements, and in which.

DETAILED DESCRIPTION

Figure 1:
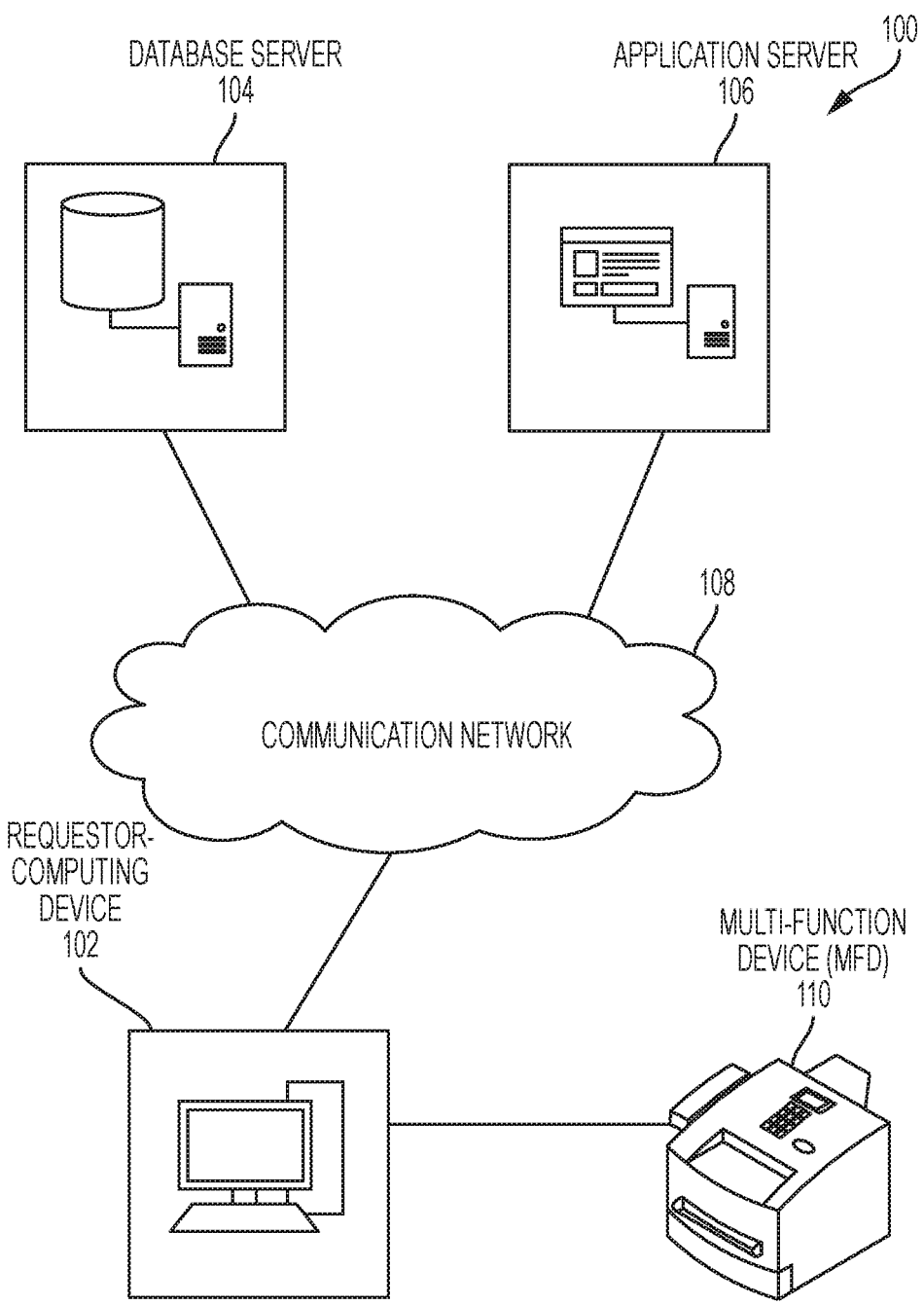
FIG. 1 is a block diagram illustrating a system environment in which various embodiments may be implemented.

The present disclosure is best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "an embodiment," "at least one embodiment," "one example," "an example," "for example," and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

Definitions

The following terms shall have, for the purposes of this application, the respective meanings set forth below.

A "computing device" refers to a device that includes one or more processors/microcontrollers and/or any other electronic components, or a device or a system that performs one or more operations according to one or more programming instructions/codes. Examples of a computing device may include, but are not limited to, a desktop computer, a laptop, a personal digital assistant (PDA), a mobile device, a smartphone, a tablet computer (e.g., iPad®, and Samsung Galaxy Tab®), and the like.

A "Multi-Function Device (MFD)" refers to an electronic device that can perform multiple functions, such as printing, scanning, copying, faxing, emailing, and the like. In an embodiment, the MFD includes a scanner and a printer for scanning and printing one or more documents (i.e., medical records [such as nursing notes], investigative reports, and other medical notes written by healthcare professionals). In an embodiment, the MFD has communication capabilities that enable the MFD to send/receive data and messages to/from other electronic device(s), in accordance with one or more communication protocols, such as, but not limited to, File Transfer Protocol, E-Mail, Server Message Block Protocol and Network File System.

A "patient" is a human being who may require medical care or treatment by a medical expert, such as a doctor. In other words, a patient is a recipient of health care services provided by a health practitioner. In an embodiment, a first patient refers to a patient who is currently under medical observation, and a second patient refers to a patient who was under medical observation in the past.

An "electronic medical record" refers to a documentation of health condition of a patient. In an embodiment, the medical record may include periodic measures of physiological parameters associated with the patient. Further, the medical record may include nursing notes documented over a specific time by a healthcare professional (such as a doctor, a nurse, a medical attender, a hospital staff, and/or the like). In an embodiment, the nursing notes may include recorded observations, administered drugs and therapies, test results, X-rays, nursing reports, investigative reports, and the like. In an embodiment, the medical record may be documented on a computing device, such as, but not limited to, a desktop computer, a laptop, a PDA, a mobile device, a smartphone, a tablet computer (e.g., iPad® and Samsung Galaxy Tab®), and the like. In an embodiment, the medical record may correspond to electronic or handwritten document(s). In case of a handwritten document (such as on a paper), the medical record may be scanned for converting it into to an electronic format.

A "nursing note" refers to a medical record that may describe a health condition of a patient and an administered or planned treatment. The nursing note may be documented by a nurse, physician, and other healthcare professionals for recording the health condition of the patient. The nursing note may comprise prescribed treatments, response to the prescribed treatments, medical diagnosis, and/or the like.

The nursing note, corresponding to the patient, may be recorded on a daily or periodic basis. Hereinafter, "nursing note" and "nursing report" may be interchangeably used.

"Historical data" refers to one or more medical records of one or more second patients who were under medical observations in the past. In an embodiment, the one or more medical records may comprise a measure of one or more physiological parameters (e.g., blood pressure, heart rate, respiratory rate, body temperature, and the like) associated with the one or more second patients. Further, the one or more medical records may comprise lab investigation data (e.g., a sodium level, a potassium level, a glucose level, and the like), diagnostics data, and other medical data associated with the one or more second patients. In an embodiment, the historical data may further comprise a health condition of each of the one or more second patients. In an embodiment, the historical data may correspond to a multivariate dataset.

A "first set of datasets" corresponds to historical data pertaining to a first patient previously examined by a medical practitioner. In an embodiment, the first set of datasets includes information pertaining to one or more measured physiological parameters.

"One or more second sets of datasets" correspond to historical data pertaining to one or more second patients who had been previously examined by a medical practitioner. In an embodiment, the one or more second sets of datasets include information pertaining to one or more measured physiological parameters that are similar to the first set of datasets.

A "first patient" refers to a patient who is currently under medical observation. In an embodiment, the first patient is the patient whose health condition is to be predicted.

A "second patient" refers to a patient who was under medical observation in the past. The second patient may have died or survived based on his/her health conditions and/or undergone treatments while he/she was under the medical observation.

A "prediction" refers to a predictive information about the one or more future tasks that may happen by analyzing the current situation or data. In an embodiment, the prediction of a patient's health may be based on the historical information.

A "clustering" refers to a collection of the one or more records with similar attributes. In an embodiment, the records provided by the nursing staff are identified in the one or more attributes, and subsequently, the one or more attributes are clustered to generate the one or more groups based on similar records. Known techniques to cluster the one or more records may include, but are not limited to, standard clustering algorithm, or similar techniques (e.g., K-Means, K-Medoids, spectral clustering, and model based algorithms such as expectation maximization [EM] for Gaussian mixture models).

A "heading" refers to a word or a group of words at the beginning of a written passage/paragraph/phrases/words, which may be indicative of a context of the passage/paragraph/phrases/words.

A "phrase" refers to a single word or a group of words that express a concept and by which it functions as a single unit in the syntax of a sentence. Various types of phrases may be noun, verb, and gerund, infinitive, appositive, participial, prepositional, and absolute.

"One or more predefined categories" refer to one or more categories utilized for separating one or more headings in one or more medical records. In an embodiment, the one or more predefined categories may be used for separating one or more words from one or more phrases documented under the one or more headings. In an embodiment, the one or more predefined categories may be defined by a user.

A "requestor" refers to a medical professional, such as, but not limited to, a doctor, a nurse, a medical attendant, a hospital staff, or any other healthcare professional.

A "sensor" refers to a device that detects/measures events or changes in quantities and provides a corresponding output, generally as an electrical or optical signal. In healthcare domain, a first type of sensors may be operable to detect and measure various biological and physical variations corresponding to the first patient. Such detected and measured signals may be recorded for further analytics. For example, biomedical sensors are used to monitor heart rate, respiration rate, pulse rate, blood pressure, and the like, of the first patient. Further, a second type of sensors may be operable to detect and measure various physical and/or chemical signals corresponding to a medical device associated with the first patient. For example, pressure sensors, temperature sensors, and humidity sensors are used to monitor and regulate gas flow and gas conditions in anesthesia machines, respirators, and ventilators.

FIG. 1 is a block diagram illustrating a system environment in which various embodiments may be implemented. FIG. 1 shows a system environment 100 that includes a requestor-computing device 102, a database server 104, an application server 106, a communication network 108, and an MFD 110. Various devices in the system environment 100 may be interconnected over the communication network 108. FIG. 1 shows, for simplicity, one requestor-computing device, such as the requestor-computing device 102, one database server, such as the database server 104, one application server, such as the application server 106, and one MFD, such as the MFD 110. However, it will be apparent to a person having ordinary skill in the art that the disclosed embodiments may also be implemented using multiple requestor-computing devices, multiple database servers, and multiple applications servers, without deviating from the scope of the disclosure.

The requestor-computing device 102 refers to a computing device that may comprise one or more processors in communication with one or more memories. The requestor-computing device 102 may be operable to execute one or more sets of instructions stored in the one or more memories. In an embodiment, the requestor-computing device 102 may be communicatively coupled with the communication network 108.

The requestor-computing device 102 may be used by a requestor to transmit/receive one or more medical records pertaining to a first patient to/from the database server 104 and/or the application server 106, over the communication network 108. The one or more medical records may correspond to scanned handwritten medical records or one or more electronic medical records. In an embodiment, the requestor-computing device 102 may transmit/receive the electronic medical records associated with the first patient to/from one or more medical devices corresponding to one or more medical departments, over the communication network 108. The one or more medical records of the first patient may include metadata such as, but not limited to, clinical notes (such as nursing notes, investigative reports, medication and allergies reports, laboratory test results, and/or the like) associated with the first patient, measure of vital parameters, and other details (such as age and weight) of the first patient.

In an embodiment, the requestor may utilize the requestor-computing device 102 to provide one or more input parameters to perform one or more operations, such as, but not limited to, capturing an image of the one or more medical records (e.g., handwritten nursing note on a paper), by an embedded image sensor. In an embodiment, the requestor-computing device 102 may be coupled with the MFD 110 that may scan the handwritten medical records, associated with the first patient. The MFD 110 may generate the corresponding electronic medical records that may be transmitted to the requestor-computing device 102. In an embodiment, the requestor-computing device 102 may comprise a display screen that may be configured to display one or more user interfaces to the requestor.

The requestor-computing device 102 may correspond to various types of computing devices, such as, but not limited to, a desktop computer, a laptop, a PDA, a mobile device, a smartphone, a tablet computer (e.g., iPad® and Samsung Galaxy Tab®), and the like.

The database server 104 may refer to a computing device that may store a repository of historical medical records of one or more second patients. In an embodiment, the database server 104 may store metadata pertaining to the historical medical records of the one or more second patients. The metadata pertaining to the historical medical records of the one or more second patients may comprise information, such as, but not limited to, one or more medical complications developed during the stay of the one or more second patients in a hospital, clinical notes (such as nursing notes, investigative reports, medication and allergies reports, laboratory test results, and/or the like) associated with the one or more second patients, measure of vital parameters, and other details (such as age and weight) of the one or more second patients. In an embodiment, the database server 104 may extract the metadata pertaining to the historical medical records from various sources, such as, but not limited to, databases of various medical organizations that may provide a rightful authentication to access the information pertaining to the one or more second patients or from publicly available databases, such as MIMIC II.

In an embodiment, the database server 104 may receive a query from the requestor-computing device 102 or the application server 106 to retrieve the metadata pertaining to the historical medical records of the one or more second patients. In an embodiment, the database server 104 may be configured to transmit or receive one or more instructions/metadata to/from one or more devices, such as the requestor-computing device 102 and the application server 106, over the communication network 108. For querying the database server 104, one or more querying languages may be utilized such as, but not limited to, structured query language (SQL), relational database query language (QUEL), data mining extensions (DMX), and so forth. Further, the database server 104 may be realized through various technologies such as, but not limited to, Microsoft® SQL server, Oracle®, and MySQL®.

The application server 106 may refer to a computing device or a software framework that may provide a generalized approach to create the application server on a computer. In an embodiment, the function of the application server 106 may be dedicated to the efficient execution of procedures, such as, but not limited to, programs, routines, or scripts stored in one or more memories for supporting applied applications.

In an embodiment, the application server 106 may be accessed by the requestor-computing device 102, over the communication network 108, to receive the one or more medical records of the first patient. Alternatively, the application server 106 may extract the one or more medical records of the first patient (that are pre-stored) from the database server 104. Further, in an embodiment, the application server 106 may transmit a query to extract the metadata pertaining to the historical medical records of the one or more second patients from the database server 104, over the communication network 108.

In an embodiment, the application server 106 may utilize a query, a program, an algorithm, or a code to segregate the historical medical records of the one or more second patients into one or more clusters. In an embodiment, the application server 106 may train one or more classifiers based on the clustered medical records. The one or more classifiers may be implemented using one or more machine learning algorithms (e.g., support vector machine [SVM]). One or more processors in the application server 106 may utilize the one or more trained classifiers to predict a health condition of the first patient based on the processing of the one or more medical records of the first patient. The application server 106 may be realized using various technologies such as, but not limited to, Java application server, .NET Framework, PHP, Base4 application server, and Appaserver. The application server 106 has been described later in conjunction with FIG. 2.

A person having ordinary skill in the art will understand that the scope of the disclosure should not be limited to the database server 104 or the application server 106 as separate entities. In an embodiment, the functionalities of the database server 104 and the application server 106 may be combined into a single server, without limiting the scope of the inventions.

The communication network 108 corresponds to a medium through which requests, content (such as one or more electronic medical records), and messages may flow between the requestor-computing device 102, the database server 104, and the application server 106. Examples of the communication network 108 may include, but are not limited to, a Wireless Fidelity (Wi-Fi) network, a Wide Area Network (WAN), a Local Area Network (LAN), or a Metropolitan Area Network (MAN). Various devices, such as the requestor-computing device 102, the database server 104, and the application server 106, may connect to the communication network 108, in accordance with various wired and wireless communication protocols, such as Transmission Control Protocol/Internet Protocol (TCP/IP), User Datagram Protocol (UDP), and 2G, 3G, or 4G communication protocols.

The multi-function device 110 may refer to an electronic device that may perform multiple functions, such as printing, scanning, copying, faxing, emailing, and the like. In an embodiment, the multi-function device 110 may include a scanner and a printer for scanning and printing one or more documents. In an embodiment, the multi-function device 110 may scan and print medical records such as nursing notes, investigative reports, medication and allergies reports, laboratory test results, and/or the like. In an embodiment, the multi-function device 110 may communicate to/from other electronic device(s) over the communication network 108, to send/receive data and messages.

A person having ordinary skill in the art will understand that the scope of the disclosure should not be limited to the MFD 110 that is coupled with the requestor-computing device 102. In an embodiment, the MFD 110 may be coupled with the database server 104 or the application server 106, without limiting the scope of the disclosure.

Figure 2:
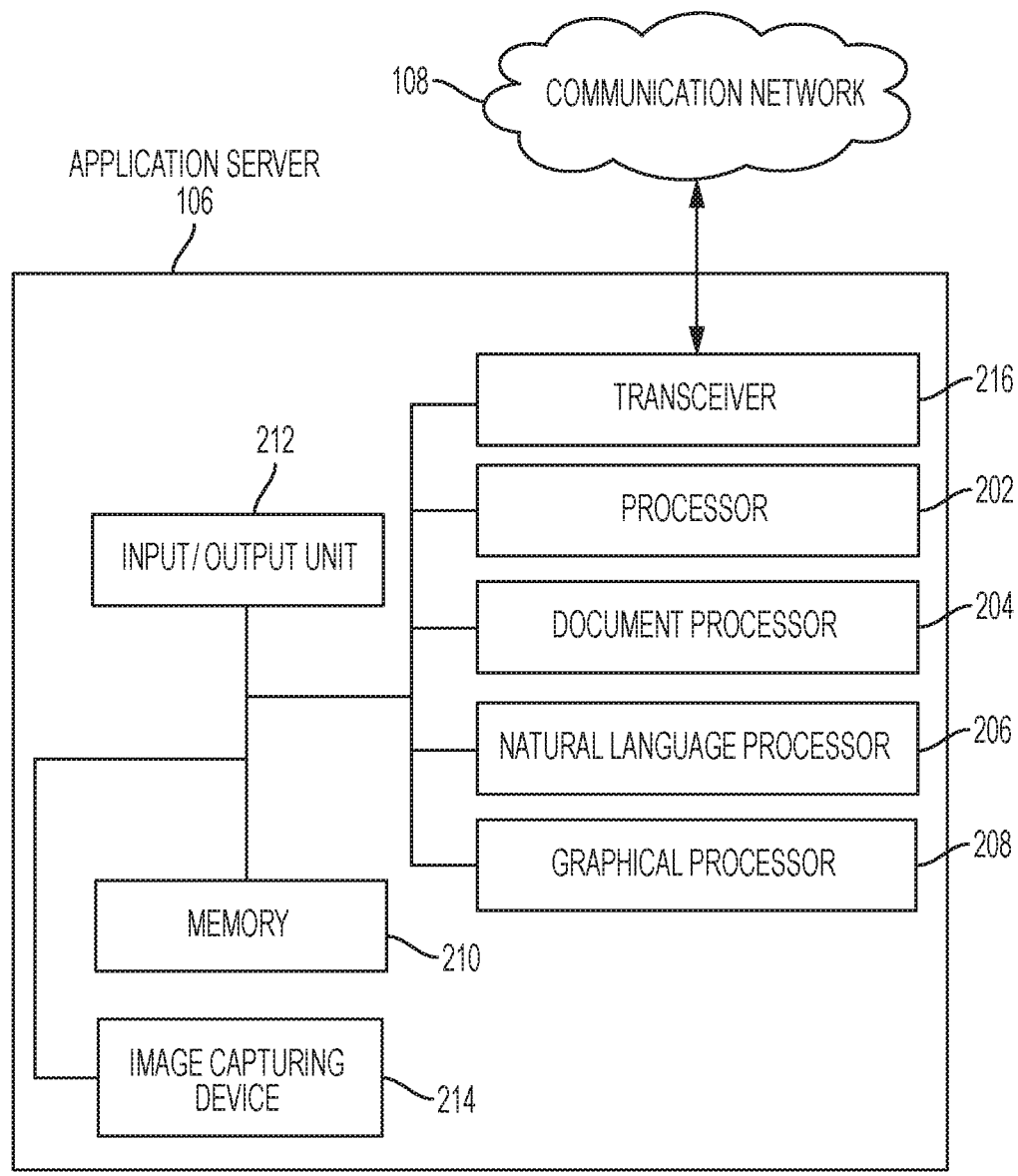
FIG. 2 is a block diagram illustrating a system for processing electronic medical records for predicting a health condition of a patient, in accordance with at least one embodiment.

FIG. 2 is a block diagram illustrating a system for processing electronic medical records for predicting the health condition of the first patient, in accordance with at least one embodiment. With reference to FIG. 2, there is shown a system that may include one or more processors, such as a processor 202, one or more document processors, such as a document processor 204, one or more natural language processor, such as a natural language processor 206, one or more graphical processors, such as a graphical processor 208, one or more memories, such as a memory 210, an input/output (I/O) device 212, an image capturing device 214, and one or more transceivers, such as a transceiver 216. The system may correspond to the application server 106 or the requestor-computing device 102, without departing from the scope of the disclosure. For the purpose of the ongoing description, the system corresponds to the application server 106.

The processor 202 may be configured to execute a set of instructions stored in the memory 210 to perform one or more operations. The processor 202 may be coupled to the memory 210, the transceiver 216, the document processor 204, the graphical processor 208 and the natural language processor 206. The processor 202 may be implemented based on a number of processor technologies known in the art. Examples of the processor 202 include, but are not limited to, an X86-based processor, a Reduced Instruction Set Computing (RISC) processor, an Application-Specific Integrated Circuit (ASIC) processor, and/or a Complex Instruction Set Computing (CISC) processor. The processor 202 may comprise one or more arithmetic logic units such as an arithmetic logic unit (ALU) and one or more control units such as a control unit. The ALU may be coupled to the control unit. The ALU may be operable to perform one or more mathematical and logical operations. The control unit may be configured to control the operation of the ALU.

In an embodiment, the processor 202 may utilize the image capturing device 214 to capture the images of the one or more handwritten medical records associated with the first patient. The processor 202 may further perform text recognition on the captured image and communicate the recognized text from the captured image to the document processor 204. Further, the processor 202 may extract one or more second sets of datasets of one or more patients from the database server 104, via the transceiver 216 and the communication network 108.

In an embodiment, the processor 202 may be configured to generate the one or more bipartite graphs, based on the first set of datasets and the two second sets of datasets. Further the processor 202 may be configured to divide the set of vertices in each bipartite graph, "V," into two disjoint sets, left and right sets, and connect an edge from every vertex in the left set of vertices to a vertex in the right set of vertices and further assign edge weights to each edge between the left set of vertices to a vertex in the right set of vertices of each of the one or more bipartite graphs.

In an embodiment, the processor 202 may be configured to determine the matching score based on at least a count of edges in the set of edges and a weight associated with each of the set of edges in the one or more bipartite graphs. Further, the processor 202 may perform a clustering of the collections, based on the determined matching score.

The document processor 204 is an electric or electronic device, or computer software application that may create structured documents. In an embodiment, the document processor 204 may be operable to analyze and process one or more documents to extract useful information. In an embodiment, the document processor 204 may be realized using one or more processors that may utilize one or more programs such as PTC Arbortext APP (formerly Advent 3B2,) Adobe FrameMaker, LyX, BroadVision QuickSilver (formerly Interleaf TPS), and Syntext Serna. In an embodiment, the document processor 204 may employ one or more image processing techniques and intelligent character recognition (ICR) techniques to process the documents.

The document processor 204 may receive the one or more first medical records of the first patient from the from the requestor computing device 102. In an embodiment, the document processor 204 may receive a request from a requestor computing device 102 to determine the first set of datasets of the first patient, based on the one or more headings and corresponding one or more phrases in the one or more first electronic medical records associated with the first patient. Further, the document processor 204 may identify the one or more headings and the one or more phrases in the one or more first electronic medical records associated with the first patient.

In an embodiment, the document processor 204 may remove non-alphabetical characters, terms with length less than "3," and/or stemming of words in the one or more headings and the one or more phrases by using various text pre-processing techniques.

The natural language processor 206 is an electric or electronic device, or computer software application that may predict the health condition of the first patient. In an embodiment, the natural language processor 206 may be realized using one or more processors that may utilize one or more programs such as PTC Arbortext APP (formerly Advent 3B2,) Adobe FrameMaker, LyX, BroadVision QuickSilver (formerly Interleaf TPS), and Syntext Serna.

The natural language processor 206 may determine a set of edges from the one or more edges based on a weight associated with each of the one or more edges. In an embodiment, the natural language processor 206, by using supervised machine learning algorithms, may predict the health condition of the first patient, based on the matching score associated with bipartite graphs in the clustered first set of data. The maximum matching collections in the one or more bipartite graphs correspond to the minimum determined distance metric.

The graphical processor 208 is an electric or electronic device, or computer software application that may create graphs. In an embodiment, the graphical processor 208 may be operable to generate graphs pertaining to first patient. In an embodiment, the graphical processor 208 may be realized using one or more processors that may utilize one or more programs such as PTC Arbortext APP (formerly Advent 3B2,) Adobe FrameMaker, LyX, BroadVision QuickSilver (formerly Interleaf TPS), and Syntext Serna.

Thereafter, the graphical processor 208 may generate one or more bipartite graphs based on the first set of datasets and the one or more second sets of dataset. In an embodiment, the graphical processor 208 may utilize extracted one or more headings and extracted one or more phrases under each of the extracted historical medical records of the one or more second patients to train the one or more classifiers.

In an embodiment, the graphical processor 208 may transmit the notification message to the requestor computing device 102 using transceiver 216 over a communication network 108. The notification message may be indicative of at least the predicted health condition of the first patient.

A person having ordinary skill in the art would understand that the scope of the disclosure is not limited to processing of the electronic form of the one or more medical records by scanning the one or more handwritten medical records such as the handwritten medical records. In an embodiment, the medical records may be documented in an electronic form at the first go. In such a scenario, the medical attender may have a tablet device that allows the medical attender to document notes. The tablet device may have an input means (touch screen of an input pen) that facilitates the medical practitioner to write notes directly on the tablet. In an embodiment, the tablet may include a software that presents a platform to the user of the tablet to write notes. Further, the written notes may be stored in the database server 104. Further, the notes may be stored in the cloud storage. Further, the scope of the disclosure is not limited to a tablet device. In an embodiment, any computing device (such as a computer, laptop, phone, Smartphone) may be used for inputting the notes.

The memory 210 may be operable to store one or more machine codes, and/or computer programs having at least one code section executable by the processor 202. The memory 210 may store one or more sets of instructions or metadata associated with one or more patients (first patient and/or one or more second patients). Some of the commonly known memory implementations include, but are not limited to, a random access memory (RAM), a read-only memory (ROM), a hard disk drive (HDD), and a secure digital (SD) card. In an embodiment, the memory 210 may include the one or more machine codes, and/or computer programs that are executable by the processor 202 to perform specific operations. It will be apparent to a person having ordinary skill in the art that the one or more instructions stored in the memory 210 enables the hardware of the system to perform the predetermined operation.

The I/O unit 212 may comprise suitable logic, circuitry, interfaces, and/or code that may be configured to receive an input or transmit an output to the requestor-computing device 104. The input/output unit 210 comprises various input and output devices that are configured to communicate with the processor 202. Examples of the input devices include, but are not limited to, a keyboard, a mouse, a joystick, a touch screen, a microphone, a camera, and/or a docking station. Examples of the output devices include, but are not limited to, a display screen and/or a speaker.

The image capturing device 214 comprises one or more image sensors that may be operable to capture images of printed text or handwritten nursing notes, or an object. The captured images may be converted to digital images by the graphical processor 208 and may get store in the memory 210. The one or more image sensors may correspond to a CMOS sensor or a CCD sensor that may be used for capturing the image of the printed text or the handwritten nursing notes. In an embodiment, the image capturing device 214 may correspond to an embedded camera or a communicatively coupled imaging device that may be utilized to capture the images of the one or more documents (such as nursing notes, investigative reports, medication and allergies reports, laboratory test results, and/or the like). Though, the image capturing device 214 is implemented within the application server 106 in FIG. 2, a person skilled in the art would appreciate the image capturing device 214 to be depicted as independent from the application server 106 without departing from the scope of the disclosure.

The requestor may utilize the MFD 110 to scan the one or more medical records of the first patient, when the one or more medical records of the first patient are not available in an electronic format. In an embodiment, the requestor may communicate a request to the application server 106 to determine the one or more medical records of the first patient, based on one or more images of the printed text or the handwritten nursing notes that may be captured by the image capturing device 214.

The transceiver 216 may be operable to communicate with the one or more devices, such as the requestor-computing device 102, and/or one or more servers, such as the database server 104 over the communication network 108. The transceiver 216 may be operable to transmit or receive the metadata to/from various components of the system environment 100. In an embodiment, the transceiver 216 is coupled to the I/O unit 212 through which the transceiver 216 may receive or transmit metadata/messages/instructions associated with the one or more patients (first patient and/or one or more second patients). In an embodiment, the I/O unit 212 may be realized through, but not limited to, an antenna, an Ethernet port, an USB port or any other port that can be configured to receive and transmit data. The transceiver 216 may receive and transmit data/messages in accordance with various communication protocols such as, TCP/IP, UDP, and 2G, 3G, or 4G.

Figure 3A:
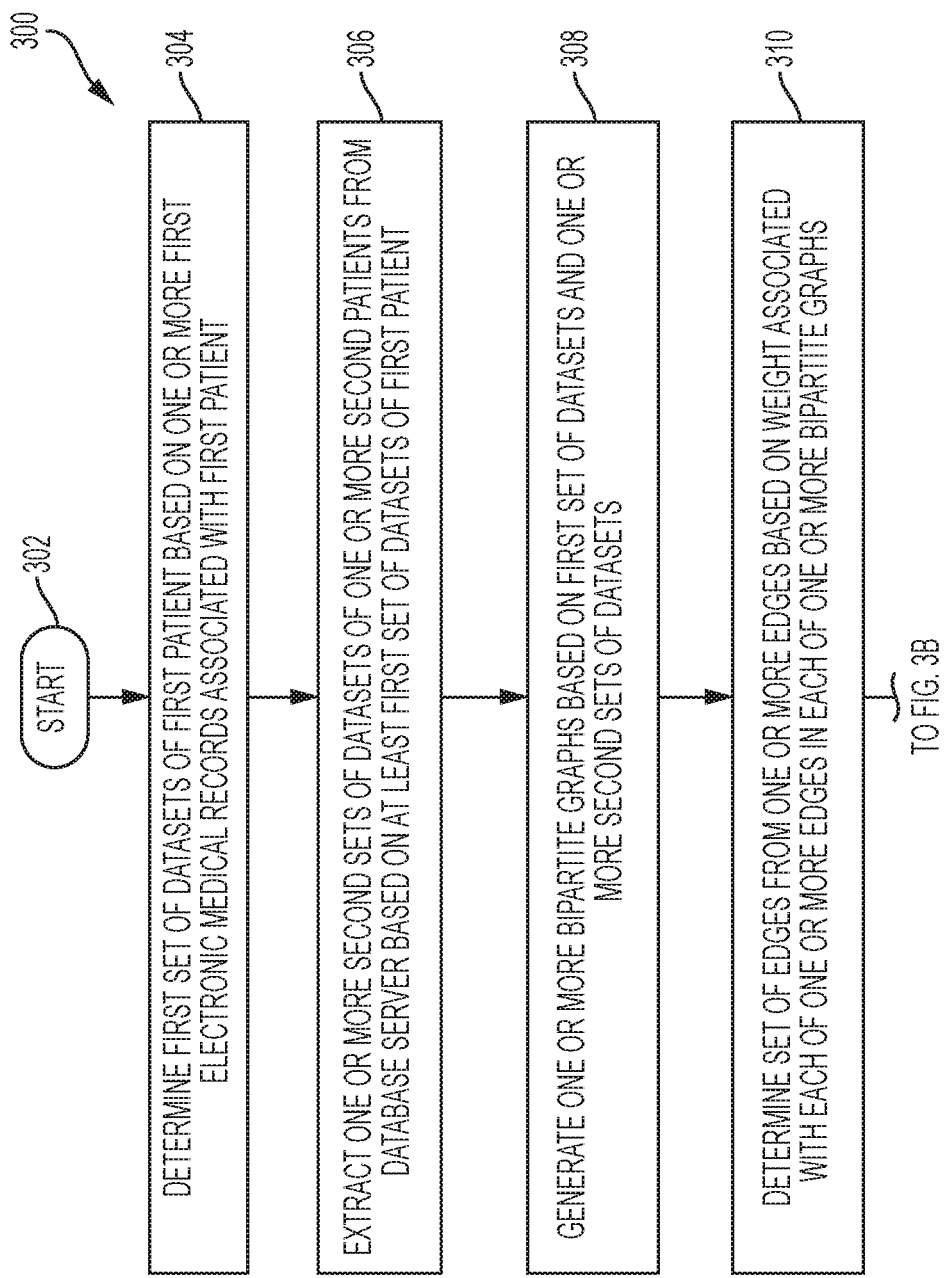
FIGS. 3A and 3B are flowcharts illustrating a method for processing electronic medical records for predicting a health condition of a patient, in accordance with at least one embodiment.
Figure 3B:
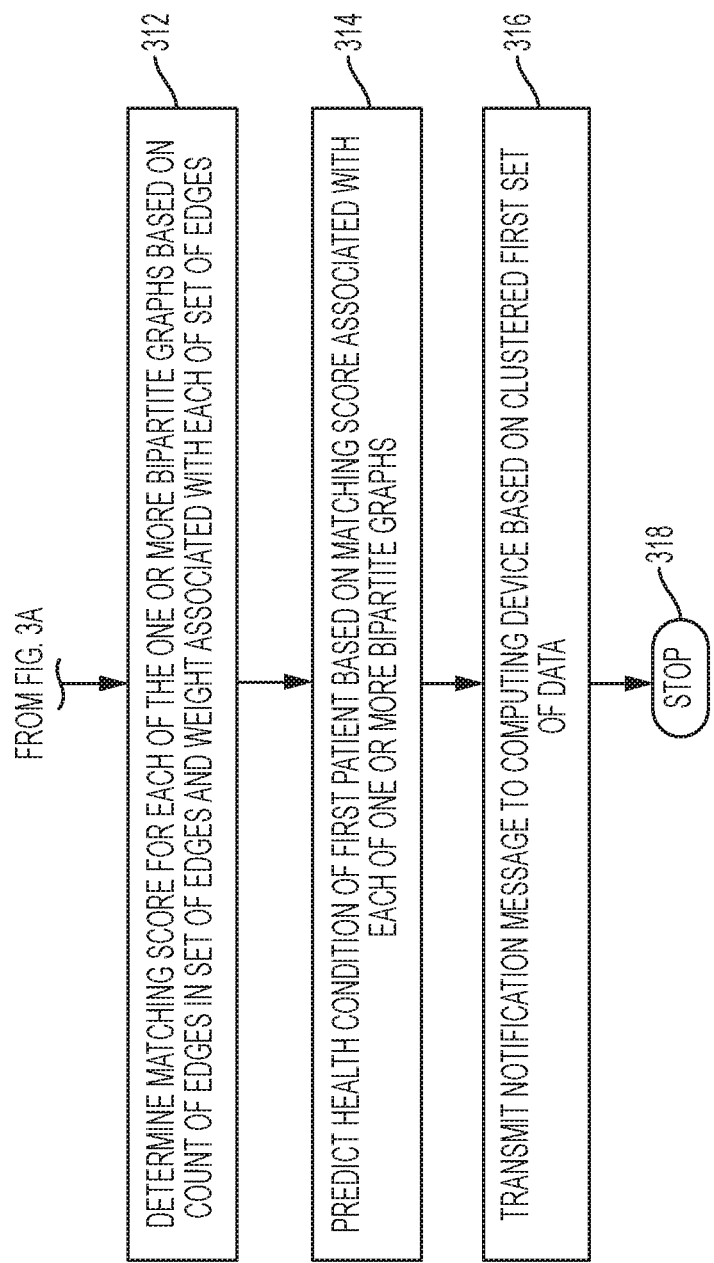

FIGS. 3A and 3B are flowcharts illustrating a method for processing electronic medical records for predicting a health condition of a patient, in accordance with an embodiment. FIGS. 3A and 3B, collectively, show a flowchart 300 that is described in conjunction with FIG. 1 and FIG. 2. The method starts at step 302 and proceeds to step 304.

At step 304, a first set of datasets of a first patient may be determined by the document processor 204, based on one or more first electronic medical records associated with the first patient. The first patient may correspond to a patient who is currently under medical observation. Further, the first set of datasets may correspond to medical data of the first patient. The one or more first medical records of the first patient may comprise, but are not limited to, one or more clinical notes, such as nursing notes, investigative reports, medication and allergies reports, laboratory test results, and/or the like, of the first patient. Thus, the one or more first medical records may correspond to one or more health-related observations of the first patient by the one or more medical attendants of a medical center. The one or more health-related observations may correspond to various physiological categories, such as cardiovascular, neurological, pulmonary, genitourinary, gastrointestinal, and endocrinal conditions of a patient, such as the first patient.

In an embodiment, the document processor 204, in conjunction with the processor 202, may receive the one or more first medical records of the first patient from the requestor-computing device 102 or the database server 104, over the communication network 108. In an embodiment, the one or more first medical records may correspond to medical records documented on the requestor-computing device 102, such as, but not limited to, a desktop computer, a laptop, a PDA, a mobile device, a smartphone, a tablet computer (e.g., iPad® and Samsung Galaxy Tab®), and the like. The requestor-computing device 102 may store the documented medical records in the database server 104 or directly communicate the one or more first medical records to the application server 106, over the communication network 108.

In an alternative embodiment, the one or more first medical records of the first patient may correspond to one or more handwritten medical records (or handwritten notes) documented by one or more healthcare professionals, such as, but not limited to, a doctor, a nurse, a medical attendant, or a hospital staff. In such a case, in an embodiment, the one or more handwritten medical records may be scanned by utilizing the MFD 110, before transmitting it to the requestor-computing device 102. Such scanned one or more handwritten medical records may be converted to one or more first electronic records by the MFD 110 and stored in the database server 104. Alternatively, the converted one or more first electronic records may be directly communicated to the application server 106 by the MFD 110, over the communication network 108. In an embodiment, the processor 202 may utilize the image-capturing device 214 to capture the images of the one or more handwritten medical records associated with the first patient. The processor 202 may further perform text recognition on the captured image and communicate the recognized text from the captured image to the document processor 204.

In an embodiment, the document processor 204 may determine the first set of datasets of the first patient, based on the one or more headings and corresponding one or more phrases in the one or more first electronic medical records associated with the first patient. The one or more headings, such as "CV," "NEURO," "PULM," "GU," "GI," and "ENDO," may correspond to respective physiological categories, such as cardiovascular, neurological, pulmonary, genitourinary, gastrointestinal, and endocrinal conditions, of a patient, such as the first patient.

The one or more phrases may correspond to a documentation of one or more health-related observations of the first patient by the one or more medical attendants of the medical center. The health-related observations may correspond to one or more physiological parameters under appropriate headings that correspond to the first set of datasets. For example, for the heading "CV," the one or more phrases may be "heart rate has dropped to 40 s," "A/V pacing wires attached," "pacer in back up mode of VVI 50 with occasional paced beats," "only aline is femoral," and the like. For the heading "PULM," the one or more phrases may be "raises thick tan or clear sputum multiple times every hour," "lungs clear," "CTS still draining fair amount of serosanginous fluid," "no airleak," and/or the like.

The document processor 204 may identify the one or more headings and the one or more phrases in the one or more first electronic medical records associated with the first patient. The document processor 204 may further determine the first set of datasets of the first patient, based on the identified one or more headings in the one or more first electronic medical records associated with the first patient. Thus, each of the first set of datasets may correspond to the one or more headings. Further, each of the first set of datasets may comprise one or more documented keywords that are representative of the one or more phrases under the corresponding heading. For example, a dataset of the first set of datasets may correspond to a heading "CARDIO." Further, the dataset may comprise one or more documented keywords, such as "heart rate has dropped to 40 s," "A/V pacing wires attached," "pacer in back up mode of VVI 50 with occasional paced beats," "only aline is femoral" under the heading "CARDIO."

For exemplary purposes, the first set, "S," may be a collection of datasets, "$S_1$," "$S_2$," and "$S_3$," represented as $\{S_1, S_2, S_3\}$. As described above, the datasets correspond to three headings, such as "CARDIO," "PULM," and "GASTROINTESTINAL." Further, each of the datasets may include a finite number of objects (i.e., a finite number of documented keywords) that correspond to one or more phrases under the corresponding headings. For example, the dataset "$S_1$," which corresponds to the heading "CARDIO," may comprise the objects "$S_{11}$," "$S_{12}$," and "$S_{13}$." The objects "$S_{11}$," "$S_{12}$," and "$S_{13}$" may correspond to the phrases, "heart rate has dropped to 40 s," "A/V pacing wires attached," and "pacer in back up mode of VVI 50 with occasional paced beats," respectively. Similarly, the dataset "$S_2$," which corresponds to the heading "PULM," may comprise the objects "$S_{21}$," "$S_{22}$," and "$S_{23}$." The objects "$S_{21}$," "$S_{22}$," and "$S_{23}$" may correspond to the phrases, "raises thick tan or clear sputum multiple times every hour," "lungs clear," "CTS still draining fair amount of serosanginous fluid," respectively. Similarly, the dataset "$S_3$," which corresponds to the heading "GASTROINTESTINAL," may comprise the objects "$S_{31}$," "$S_{32}$," and "$S_{33}$." A person having ordinary skill in the art will understand that the scope of the abovementioned example is for illustrative purpose and should not be construed to limit the scope of the disclosure.

In an embodiment, the one or more headings and/or the one or more phrases in the one or more first electronic medical records are expressed differently by different healthcare professionals. For example, "CARDIOLOGY," "CV," "CARD" all correspond to the same heading, "CARDIO." In such a case, the document processor 204 may refer to a medical dictionary to identify one or more synonymous terms and semantics for the one or more headings and the one or more phrases. Accordingly, the document processor 204 may determine the first set of datasets of the first patient. In an embodiment, prior to the formation of the first set of datasets, the document processor 204 may remove non-alphabetical characters, terms with length less than "3," and/or stemming of words in the one or more headings and the one or more phrases by using various text pre-processing techniques.

At step 306, one or more of the one or more second sets of datasets of the one or more second patients are extracted from the database server 104, based on at least the first set of datasets of the first patient. The one or more second patients may correspond to one or more patients who were under medical observations in the past. Further, the second set of datasets may correspond to historical data of the one or more second patients. In an embodiment, the processor 202 may extract the one or more second sets of datasets of one or more second patients from the database server 104 based on a comparison with at least the first set of datasets of the first patient.

In an embodiment, the processor 202 may extract the one or more second sets of datasets associated with the one or more second patients by sending a database query to the database server 104, via the transceiver 216 and the communication network 108. In an embodiment, prior to receiving the database query, the database server 104 may already store the historical medical records associated with the one or more second patients. The historical medical records of the one or more second patients may include metadata, such as, but not limited to, clinical notes such as nursing notes, investigative reports, medication and allergies reports, laboratory test results, and/or the like of the one or more second patients. The document processor 204 may determine one or more seconds sets of datasets of the one or more second patients, based on the historical medical records associated with the one or more second patients in the database server 104.

In an embodiment, the document processor 204 may determine the one or more second sets of datasets of the one or more second patients, based on the one or more headings and corresponding one or more phrases in the historical medical records associated with the one or more second patients. As described above with regards to the determination of the first set of datasets, the document processor 204 may determine the one or more second sets of datasets of the one or more second patients. The processor 202 may perform the comparison based on matching between the one or more headings and/or one or more phrases in the first set of datasets associated with the first patient and the one or more headings and/or one or more phrases in the one or more second sets of datasets associated with the one or more second patients. For example, the processor 202 may extract two second sets of datasets of two second patients from database server 104, based on the common headings, "CARDIO," "PULM," and "GASTROINTESTINAL."

For exemplary purposes, one of the one or more second sets, "T," may be a collection of datasets, "$T_1$," "$T_2$," and "$T_3$," represented as $\{T_1, T_2, T_3\}$. The datasets "$T_1$," "$T_2$," and "$T_3$" correspond to three headings, such as "CARDIO," "PULM," and "GASTROINTESTINAL." Further, each of the datasets may include a finite number of objects that correspond to one or more phrases under the corresponding headings. For example, the dataset "$T_1$," that corresponds to the heading "CARDIO," may comprise the objects "$T_{11}$," "$T_{12}$," and "$T_{13}$." The objects "$T_{11}$," "$T_{12}$," and "$T_{13}$" may correspond to the phrases, "pulse rate is up," "occasional PVCs," and "Milrenone decreased," respectively. Similarly, the dataset "$T_2$," that corresponds to the heading "PULM," may comprise the objects "$T_{21}$," "$S_{22}$," and "$T_{23}$." The objects "$T_{21}$," "$S_{22}$," and "$T_{23}$" may correspond to the phrases, "good sats," "lungs clear," and "severe coughing," respectively. Similarly, the dataset "$T_3$" that corresponds to the heading "GASTROINTESTINAL," may comprise the objects "$S_{31}$," "$T_{32}$," and "$S_{33}$." The objects "$S_{31}$," "$T_{32}$," and "$S_{33}$" may correspond to the phrases, "active bowel movement," "loss of appetite," and "no BM," respectively. It may be observed that the objects "$S_{22}$," "$S_{31}$," and "$S_{33}$" are common between the second set, "T," and the first set, "S."

Similarly, another of the one or more second sets, "U," may be a collection of datasets, "$U_1$," "$U_2$," and "$U_3$," represented as $\{U_1, U_2, U_3\}$. The datasets "$U_1$," "$U_2$," and "$U_3$" correspond to three headings, such as "CARDIO," "PULM," and "GASTROINTESTINAL." Further, each the datasets may include a finite number of objects that correspond to one or more phrases under the corresponding headings. For example, the dataset "$U_1$," that corresponds to the heading "CARDIO," may comprise the objects "$U_{11}$," "$U_{12}$," and "$U_{13}$." The objects "$U_{11}$," "$U_{12}$," and "$U_{13}$" may correspond to the phrases, "heart rate has dropped to 40 s," "A/V pacing wires attached," and "pacer in back up mode of VVI 50 with occasional paced beats," respectively. Similarly, the dataset "$U_2$," that corresponds to the heading "PULM," may comprise the objects "$U_{21}$," "$U_{22}$," and "$U_{23}$." The objects "$U_{21}$," "$U_{22}$," and "$U_{23}$" may correspond to the phrases, "raises thick tan or clear sputum multiple times every hour," "lungs clear," "CTS still draining fair amount of serosanguinous fluid," respectively. Similarly, the dataset "$U_3$" that corresponds to the heading "GASTROINTESTINAL," may comprise the objects "$U_{31}$," "$U_{32}$," and "$U_{33}$." It may be observed that the objects in the second set $\{U_1, U_2, U_3\}$ are completely different from the data in the first set $\{S_1, S_2, S_3\}$. It may be observed that the objects in the second set, "U," are completely different from the objects in the first set, "S."

A person having ordinary skill in the art will understand that the scope of the abovementioned example is for illustrative purpose and should not be construed to limit the scope of the disclosure.

At step 308, one or more bipartite graphs are generated, based on the first set of datasets and the one or more second sets of datasets. In an embodiment, the graphical processor 208 may be configured to generate the one or more bipartite graphs, based on the first set of datasets and the one or more second sets of datasets. For example, the graphical processor 208 may be configured to generate two bipartite graphs, "$G_1$ (S, T)" and "$G_2$ (S, U)," based on the first set, "S," of datasets and the two second sets, "T" and "U," of datasets.

Each bipartite graph comprises a set of vertices, "V," and a set of edges, "E." For each bipartite graph, the processor 202 may divide the set of vertices, "V," into two disjoint sets, left and right sets, and connect an edge from every vertex in the left set of vertices to a vertex in the right set of vertices. For example, in the bipartite graph, "$G_1$ (S, T)," the sets of vertices may comprise the first set, "S," of datasets that corresponds to the left set, and the second set, "T," of datasets that may correspond to the right set in the bipartite graph, "$G_1$ (S, T)." Similarly, in the bipartite graph, "$G_2$ (S, U)," the sets of vertices may comprise the first set, "S," of datasets that corresponds to the left set, and the second set, "U," of datasets that corresponds to the right set in the bipartite graph, "$G_2$ (S, U)."

In an embodiment, the processor 202 may be further configured to assign edge weights to each edge between the left set of vertices to a vertex in the right set of vertices of each of the one or more bipartite graphs. The edge weights may be assigned to each edge based on one or more known distance metrics, such as Jaccard distance metric, between underlying datasets. For example, the processor 202 may be configured to determine the distance, such as "$d_s$," between the left vertices and right vertices of the two bipartite graphs, "$G_1$ (S, T)" and "$G_2$ (S, U)." The distance, "$d_s$," may be determined based on the following mathematical expressions (1) and (2):

$$d_s(S_i, T_i) = 1 - (|(S_i \cap T_i)|/|(S_i \cup T_i)|) \qquad (1)$$

$$d_s(S_i, U_i) = 1 - (|(S_i \cap T_i)|/|(S_i \cup T_i)|) \qquad (2)$$

where, $d_s$ ($S_i, T_i$) corresponds to the distance between the left vertices that correspond to the first set "S" and right vertices that correspond to the second set "T" in the bipartite graph "$G_1$ (S, T)"; and $d_s$ ($S_i, U_i$) corresponds to the distance between the left vertices that correspond to the first set "S" and right vertices that correspond to the second set "U" in the bipartite graph "$G_2$ (S, T)."

At step 310, a set of edges from the one or more edges in the one or more bipartite graphs may be determined, based on a weight associated with each of the one or more edges. In accordance with an embodiment, the processor 202 may determine the set of edges from the one or more edges in each of the one or more bipartite graphs. The set of edges may correspond to minimum distance, or in other words, maximum similarity between the corresponding left and right vertices in the one or more bipartite graphs. Another set of edges may correspond to greater distance, or in other words, less similarity between the corresponding left and right vertices in the one or more bipartite graphs.

In accordance with the example, both of the bipartite graphs "$G_1$ (S, T)" and "$G_2$ (S, U)" may comprise one or more edges associated with corresponding weights that correspond to the determined distance values. The bipartite graph "$G_1$ (S, T)" may comprise a first set of edges that may be represented by solid lines with corresponding weights and a second set of edges that may be represented by dashed lines with corresponding weights, as described in further detail in FIG. 4.

A person having ordinary skill in the art will understand that the scope of the abovementioned example is for illustrative purpose and should not be construed to limit the scope of the disclosure.

At step 312, a matching score may be determined based on at least a count of edges in the set of edges and a weight associated with each of the set of edges. In an embodiment, the processor 202 may be configured to determine the matching score based on at least the count of edges in the set of edges and the weight associated with each of the set of edges in the one or more bipartite graphs. The matching score may correspond to a real number, to which a pair of collections is mapped, which defines a distance between the two collections in the pair of collections. For example, the minimum weight maximum matching of a bipartite graph, such as "$G_1$ (S, T)" that comprises edges, "n (M)," and weight, "w (M)," may be represented by "M." The distance, d (S, T), between the collections "S" and "T," may correspond to a normalized weight "w (M)/n (M)" of the minimum weight matching "M." The matching score for the bipartite graph, "$G_1$ (S, T)," may correspond to the distance, d (S, T).

In an embodiment, pairwise distances, as minimum weight matching between each pair of collections in the one or more bipartite graphs, may be computed. The computation may be based on a matching that may be a set of pairwise non-adjacent edges such that no two edges share a common vertex. A maximum matching may be a matching that contains the largest possible number of edges in the bipartite graph. The weight of the matching may be the sum of weights of edges in the matching. Thus the minimum weight maximum matching is the maximum matching with the minimum weight. It can be computed by Hungarian algorithm in $O(V^2E)$ time, where "V" is the set of vertices and "E" is the set of edges in a graph. In bipartite graphs, the minimum weight maximum matching problem can be solved in $O(V^3)$ time.

For exemplary purposes, the matching score for the bipartite graph, "$G_1$ (S, T)" may be less than the matching score for the bipartite graph, "$G_1$ (S, U)" due to higher similarity between the vertices of the bipartite graph, "$G_1$ (S, T)." A person having ordinary skill in the art will understand that the scope of the abovementioned example is for illustrative purpose and should not be construed to limit the scope of the disclosure.

At step 314, based on the determined distance metric (or the matching score), a clustering of the collections may be performed. In an embodiment, the processor 202 may perform a clustering of the collections, such as the first set of datasets, based on the determined distance metric (or the matching score). The first set of datasets may be clustered into one of one or more predefined categories by utilizing one or more distance-based clustering algorithms, such as K-Means, K-Medoids, PAM clustering, model-based algorithms like EM for Gaussian Mixture Models, and density-based algorithms like DBSCAN.

For exemplary purposes, the first set, "S," of datasets may be clustered with the second set "T," of datasets due to higher matching score for the bipartite graph, "$G_1$ (S, T)" than the bipartite graph, "$G_2$ (S, U)." A person having ordinary skill in the art will understand that the scope of the abovementioned example is for illustrative purpose and should not be construed to limit the scope of the disclosure.

At step 316, the health condition of the first patient is predicted, based on the matching score associated with bipartite graphs in the clustered first set of data. In an embodiment, the natural language processor 206, by using supervised machine learning algorithms, may predict the health condition of the first patient, based on the matching score associated with bipartite graphs in the clustered first set of data. The maximum matching collections in the one or more bipartite graphs correspond to the minimum determined distance metric. Thereafter, the processor 202 may predict the health condition of the first patient based on the analysis of at least one of, but not limited to, the dataset in the bipartite graph that correspond to the minimum determined distance metric. The dataset corresponds to historic medical records of a second patient. Accordingly, the processor 202 may predict morbidity, a length of hospital stay, and a risk of acquiring complications by the first patient who is under medical observation.

For exemplary purposes, the first set, "S," of datasets may be clustered with the second set "T," of datasets due to higher matching score for the bipartite graph, "$G_1$ (S, T)" than the bipartite graph, "$G_2$ (S, U)." Further, for the pulmonary physiological disorder, the second set "T" indicates that the corresponding second patient was administered a nebulizer. Accordingly, the natural language processor 206 may predict that the first patient may also require nebulization.

At step 318, a notification message is transmitted to the requestor-computing device 102. In an embodiment, the graphical processor 208 may transmit the notification message to the requestor-computing device 102 using transceiver 216 over a communication network 108. The notification message may be indicative of at least the predicted health condition of the first patient. In an embodiment, the notification message, such as "NEBULIZATION MAY BE REQUIRED," may be displayed on a screen integrated with the requestor-computing device 102.

A person having ordinary skill in the art would understand that the scope of the disclosure should not be limited to the processing of electronic health records for prediction of the health condition of the first patient who is under medical observation in the ICU. In an embodiment, the disclosed method and system may be utilized to process the electronic medical records to predict the health condition of the first patient who is undergoing treatment (not necessarily in the ICU) in the hospital. In another embodiment, the disclosed method and system may be utilized to process the electronic medical records to predict the health condition of the first patient who is undergoing treatment at a second place such as, but not limited to, a medical camp, his/her house, or like.

Various embodiments of the disclosure lead to the processing of electronic medical records for predicting the health condition of a patient who is under medical observation. The disclosed method utilizes the processing of one or more medical records of the patient such as the text sources of information (nursing notes, investigative reports, etc.) to predict the postoperative health condition of the patient. The disclosed method further utilizes the statistical features extracted from the one or more vital signs (blood pressure, heart rate, respiratory rate, etc.) to predict the health condition of the patient. The disclosed system is a real time clinical surveillance system that attempts to identify emerging complications (e.g., stroke, urinary tract infections, myocardial infarctions, etc.) for the patient under medical observation, so that a risk of complication/medical emergency can be identified and treated before the patient is discharged from the hospital.

Figure 4:
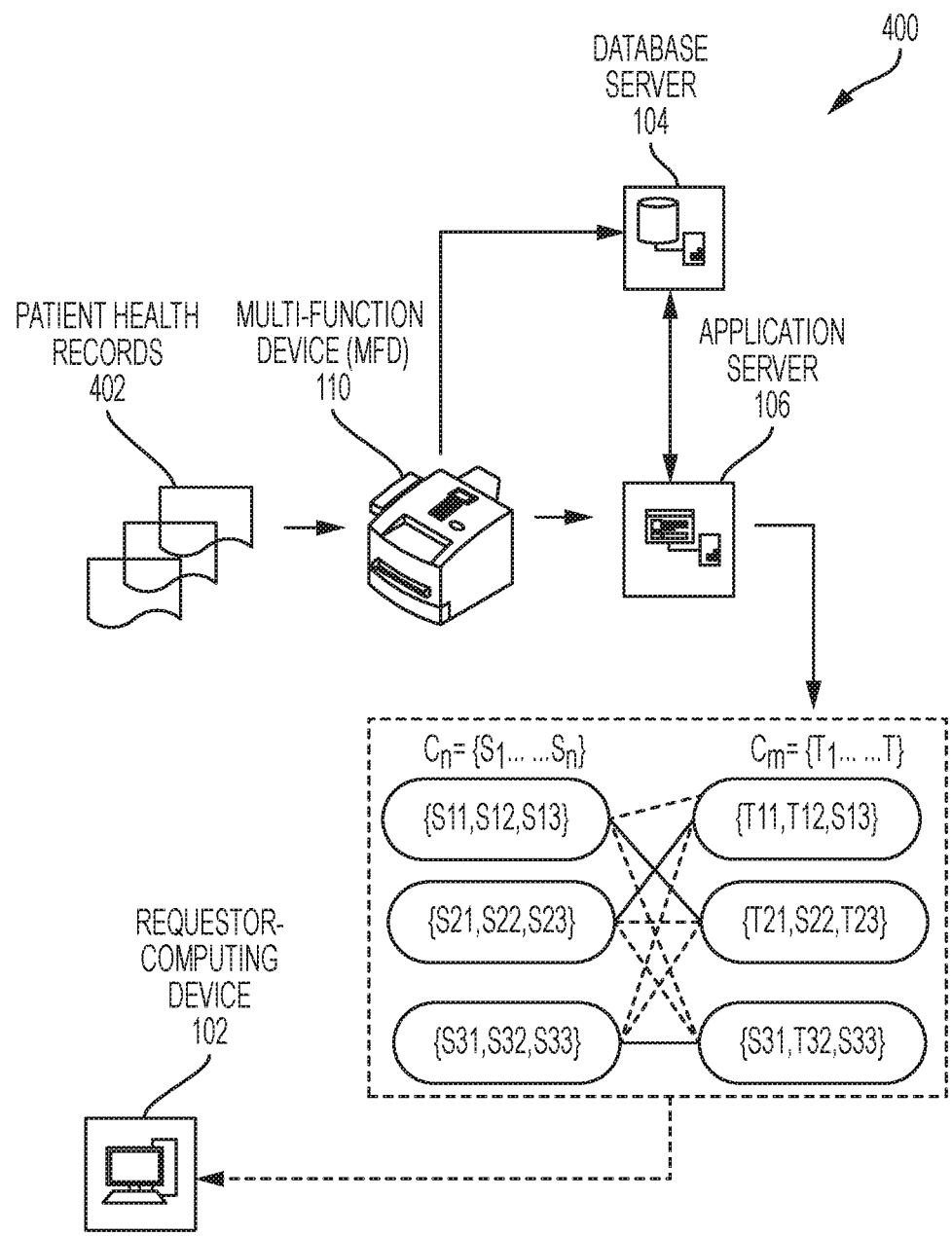
FIG. 4 is an exemplary scenario for predicting a health condition of a patient, in accordance with at least one embodiment.

FIG. 4 is an exemplary scenario for predicting a health condition of a patient using system environment 400. The requestor may generate a request for health prediction of a first patient using requestor-computing device 102. Prior to generating the request, the requestor may scan one or more medical records 402 using an MFD 110 to generate an electronic format of the one or more medical records 402. Further, the processor 202 may extract the one or more second sets of one or more second patients by sending a database query to the database server, based on at least the first set of datasets of the first patient. Afterwards, the graphical processor 208, based on pre-determined pseudo codes and algorithms, generates one or more bipartite graphs.

Each bipartite graph comprises a set of vertices, "V," and a set of edges, "E." For each bipartite graph, the processor 202 may divide the set of vertices, "V," into two disjoint sets, left and right, and connect an edge from every vertex in the left set of vertices to a vertex in the right set of vertices. For example, in the bipartite graph, "$G_1$ (S, T)," the sets of vertices may comprise the first set, "S," of datasets that corresponds to the left set, and the second set, "T," of datasets that may correspond to the right set in the bipartite graph, "$G_1$ (S, T)." Further, the processor 202 may determine the distance between the left set of vertices "$S_1$," "$S_2$," and "$S_3$" and the right set of vertices "$T_1$," "$T_2$," and "$T_3$." As explained in FIGS. 3A and 3B, "$S_1$" and "$T_1$" correspond to the heading "CARDIO," "$S_2$" and "$T_2$" correspond to the heading "PULM," and "$S_3$" and "$T_3$" correspond to the heading "GASTROINTESTINAL." The distance between the left set of vertices "$S_1$," "$S_2$," and "$S_3$" and the right set of vertices "$T_1$," "$T_2$," and "$T_3$" may correspond to the set of edges, "E." The distance may be represented as "$d_s$" and may be computed for each of the set of edges based on the mathematical expression (1) (FIGS. 3A and 3B), as follows:

$$d_s(S_1,T_1)=1-(|(S_1 \cap T_1)|/|(S_1 \cup T_1)|)=1-(0/6)=1$$

where,
($|(S_1 \cap T_1)|$) corresponds to the intersection of dataset "$S_1$" and "$T_1$," which is null; and
($|(S_1 \cup T_1)|$) corresponds to the union of dataset "$S_1$" and "$T_1$," which is 6.

$$d_s(S_1,T_2)=1-(|(S_1 \cap T_2)|/|(S_1 \cup T_2)|)=1-(0/6)=1$$

where,
($|(S_1 \cap T_2)|$) corresponds to intersection of dataset "$S_1$" and "$T_2$" which is null; and
($|(S_1 \cup T_2)|$) corresponds to union of dataset "$S_1$" and "$T_2$," which is 6.

$$d_s(S_1,T_3)=1-(|(S_1 \cap T_3)|/|(S_1 \cup T_3)|)=1-(0/6)=1$$

where,
($|(S_1 \cap T_3)|$) corresponds to the intersection of dataset "$S_1$" and "$T_3$" which is null; and
($|(S_1 \cup T_3)|$) corresponds to the union of dataset "$S_1$" and "$T_3$," which is 6.

$$d_s(S_2,T_1)=1-(|(S_2 \cap T_1)|/|(S_2 \cup T_1)|)=1-(0/6)=1$$

where,
($|(S_2 \cap T_1)|$) corresponds to the intersection of dataset "$S_2$" and "$T_1$," which is null; and
($|(S_2 \cup T_1)|$) corresponds to the union of dataset "$S_2$" and "$T_1$," which is 6.

$$d_s(S_2,T_1)=1-(|(S_2 \cap T_2)|/|(S_2 \cup T_2)|)=1-(1/5)=0.8$$

where,
($|(S_2 \cap T_2)|$) corresponds to the intersection of dataset "$S_2$" and "$T_2$," which is one as the object S22 is same in dataset $S_2$ and $T_2$; and
($|(S_2 \cup T_2)|$) corresponds to the union of dataset "$S_2$" and "$T_2$," which is 5.

$$d_s(S_2,T_3)=1-(|(S_2 \cap T_3)|/|(S_2 \cup T_3)|)=1-(0/6)=1$$

where,
($|(S_2 \cap T_3)|$) corresponds to the intersection of dataset "$S_2$" and "$T_3$," which is null; and $$d_s(S_3,T_1)=1-(|(S_3 \cap T_1)|/|(S_3 \cup T_1)|)=1-(0/6)=1$$

where,
($|(S_3 \cap T_1)|$) corresponds to the intersection of dataset "$S_3$" and "$T_1$," which is null; and
($|(S_3 \cup T_1)|$) corresponds to the union of dataset "$S_3$" and "$T_1$," which is 6.

$$d_s(S_3,T_2)=1-(|(S_3 \cap T_2)|/|(S_3 \cup T_2)|)=1-(0/6)=1$$

where,
($|(S_3 \cap T_2)|$) corresponds to the intersection of dataset "$S_3$" and "$T_2$," which is null; and
($|(S_3 \cup T_2)|$) corresponds to the union of dataset "$S_3$" and "$T_2$," which is 6.

$$d_s(S_3,T_3)=1-(|(S_3 \cap T_3)|/|(S_3 \cup T_3)|)=1-(2/4)=0.5$$

where,
($|(S_3 \cap T_3)|$) corresponds to intersection of dataset "$S_3$" and "$T_3$," which is 2 as the objects S31 and S33 in the datasets are similar; and
($|(S_3 \cup T_3)|$) corresponds to the union of dataset "$S_3$" and "$T_3$," which is 4.

Further, the processor 202 may determine the minimum weight maximum matching in a bipartite graph, such as "$G_1$ (S, T)" that comprises edges "n (M)," and weight, "w (M)," may be represented by "M." The distance, d (S, T), between the collections "S" and "T," may correspond to a normalized weight "w (M)/n (M)" of the minimum weight matching "M." The matching score for the bipartite graph, "$G_1$ (S, T)," may correspond to the distance, d (S, T) and may be computed by $$d=w(M)/n(M)\ d=0.5/9=0.055$$

where,
w (M) corresponds to minimum weight of edge, and
n (M) corresponds to total number of edges.

Similarly, another of the one or more second sets, "U," may be a collection of datasets, "$U_1$," "$U_2$," and "$U_3$," represented as {$U_1$, $U_2$, $U_3$}. The datasets "$U_1$," "$U_2$," and "$U_3$" correspond to three headings, such as "CARDIO," "PULM," and "GASTROINTESTINAL." Further, each of the datasets may include a finite number of objects that correspond to one or more phrases under the corresponding headings. For example, the dataset "$U_1$," that corresponds to the heading "CARDIO," may comprise the objects "$U_{11}$," "$U_{12}$," and "$U_{13}$." Similarly, the dataset "$U_2$" that corresponds to the heading "PULM," may comprise the objects "$U_{21}$," "$U_{22}$," and "$U_{23}$." Similarly, the dataset "$U_3$" that corresponds to the heading "GASTROINTESTINAL," may comprise the objects "$U_{31}$," "$U_{32}$," and "$U_{33}$." It may be observed that the objects in the second set {$U_1$, $U_2$, U3} are completely different from the data in the first set {$S_1$, $S_2$, $S_3$}. It may be observed that the objects in the second set, "U," are completely different from the objects in the first set, "S." Further, the processor 202 may determine the distance between the left set of vertices "$S_1$," "$S_2$," and "$S_3$," and the right set of vertices "$U_1$," "$U_2$," and "$U_3$." As explained in FIGS. 3A and 3B, "$S_1$" and "$U_1$" correspond to the heading "CARDIO," "$S_2$" and "$U_2$" correspond to the heading "PULM," and "$S_3$" and "$U_3$" correspond to the heading "GASTROINTESTINAL." The distance between the left set of vertices "$S_1$," "$S_2$," and "$S_3$," and the right set of vertices "$U_1$," "$U_2$," and "$U_3$" may correspond to the set of edges, "E." The distance may be represented as "$d_s$" and may be computed for each of the set of edges based on the mathematical expression (2) (FIGS. 3A and 3B), as follows $$d_s(S_1, U_1) = 1 - (|(S_1 \cap U_1)|/(|S_1 \cup U_1|)) = 1 - (0/6) = 1$$

where,
$(|S_1 \cap U_1|)$ corresponds to the intersection of dataset "$S_1$" and "$U_1$," which is null; and
$(|S_1 \cup U_1|)$ corresponds to the union of dataset "$S_1$" and "$U_1$," which is 6.

$$d_s(S_1, U_2) = 1 - (|(S_1 \cap U_2)|/(|S_1 \cup U_2|)) = 1 - (0/6) = 1$$

where,
$(|S_1 \cap U_2|)$ corresponds to intersection of dataset "$S_1$" and "$U_2$," which is null; and
$(|S_1 \cup U_2|)$ corresponds to the union of dataset "$S_1$" and "$U_2$," which is 6.

$$d_s(S_1, U_3) = 1 - (|(S_1 \cap U_3)|/(|S_1 \cup U_3|)) = 1 - (0/6) = 1$$

where,
$(|S_1 \cap U_3|)$ corresponds to the intersection of dataset "$S_1$" and "$U_3$," which is null; and
$(|S_1 \cup U_3|)$ corresponds to the union of dataset "$S_1$" and "$U_3$," which is 6.

$$d_s(S_2, U_1) = 1 - (|(S_2 \cap U_1)|/(|S_2 \cup U_1|)) = 1 - (0/6) = 1$$

where,
$(|S_2 \cap U_1|)$ corresponds to the intersection of dataset "$S_2$" and "$U_1$," which is null; and
$(|S_2 \cup U_1|)$ corresponds to the union of dataset "$S_2$" and "$U_1$," which is 6.

$$d_s(S_2, U_2) = 1 - (|(S_2 \cap U_2)|/(|S_2 \cup U_2|)) = 1 - (0/6) = 1$$

where,
$(|S_2 \cap U_2|)$ corresponds to the intersection of dataset "$S_2$" and "$U_2$," which is null; and
$(|S_2 \cup U_2|)$ corresponds to the union of dataset "$S_2$" and "$U_2$," which is 6.

$$d_s(S_2, U_3) = 1 - (|(S_2 \cap U_3)|/(|S_2 \cup U_3|)) = 1 - (0/6) = 1$$

where,
$(|S_2 \cap U_3|)$ corresponds to the intersection of dataset "$S_2$" and "$U_3$," which is null; and
$(|S_2 \cup U_3|)$ corresponds to the union of dataset "$S_2$" and "$U_3$," which is 6.

$$d_s(S_3, U_1) = 1 - (|(S_3 \cap U_1)|/(|S_3 \cup U_1|)) = 1 - (0/6) = 1$$

where,
$(|S_3 \cap U_1|)$ corresponds to the intersection of dataset "$S_3$" and "$U_1$," which is null; and
$(|S_3 \cup U_1|)$ corresponds to the union of dataset "$S_3$" and "$U_1$," which is 6.

$$d_s(S_3, U_2) = 1 - (|(S_3 \cap U_2)|/(|S_3 \cup U_2|)) = 1 - (0/6) = 1$$

where,
$(|S_3 \cap U_2|)$ corresponds to the intersection of dataset "$S_3$" and "$U_2$," which is null; and
$(|S_3 \cup U_2|)$ corresponds to the union of dataset "$S_3$" and "$U_2$," which is 6.

$$d_s(S_3, U_3) = 1 - (|(S_3 \cap U_3)|/(|S_3 \cup U_3|)) = 1 - (1/5) = 0.8$$

where,
$(|S_3 \cap U_3|)$ corresponds to the intersection of dataset "$S_3$" and "$U_3$," which is one as the object S33 is same in dataset $S_3$ and $U_3$; and
$(|S_3 \cup U_3|)$ corresponds to the union of dataset "$S_3$" and "$U_3$," which is 5.

The matching score for the bipartite graph, "$G_2$ (S, U)," may correspond to the distance, d (S, U) and may be computed by $$d = w(M)/n(M) \quad d = 0.8/9 = 0.088$$

where,
w (M) corresponds to minimum weight of edge, and
n (M) corresponds to the total number of edges.

Further, the processor 202 may compare the matching score for the bipartite graph, "$G_1$ (S, T)" and "$G_2$ (S, U)" and may determine that the matching score of the bipartite graph, "$G_1$ (S, T)" is less and therefore due to higher similarity between the vertices of the bipartite graph, "$G_1$ (S, T)" and the first set, "S," of datasets may be clustered with the second set "T," of datasets due to higher matching score for the bipartite graph, "$G_1$ (S, T)" than the bipartite graph, "$G_2$ (S, U)." Further, the natural language processor 206, by using supervised machine learning algorithms, may predict the health condition of the first patient, based on the determined minimum distance associated with bipartite graph "$G_1$ (S, T)" and the graphical processor 208 may transmit the notification message to the requestor computing device 102 using transceiver 216 over a communication network 108.

The disclosed embodiments encompass numerous advantages. The method discloses a processing of electronic medical records for predicting a health condition of the first patient. The method discloses clustering the datasets related to one or more patients to predict the health condition of the first patient by minimum weight and maximum match technique. Further, the disclosed method may be utilized in the healthcare industry to predict the health of the patients. Based on at least the prediction of the health condition, precautionary and necessary steps may be taken to reduce the risk of deaths in the patients. The disclosed classification method may further be utilized in the area of risk assessment, fraud detection and analysis of complex data.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices, or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to, "C," "C++," "Visual C++," Java, and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various embodiments of the methods and systems for processing electronic medical records for predicting a health condition of a patient have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules and is not limited to any particular computer hardware, software, middleware, firmware, microcode, or the like.

The claims can encompass embodiments for hardware, software, or a combination thereof.

It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

What is claimed is:

1. A method for processing electronic medical records for predicting a health condition of a patient, the method comprising:
   extracting information from one or more first electronic medical records of a first patient to produce a first set of datasets,
   the one or more first electronic medical records being received from a computing device over a communication network, and
   the first set of datasets including one or more first categories and one or more first objects within each first category;
   extracting one or more second sets of datasets of one or more second patients from a database server based on at least the first set of datasets of the first patient,
   the one or more second set of datasets each including one or more second categories and one or more second objects within each second category;
   generating one or more bipartite graphs based on the first set of datasets and the one or more second sets of datasets, wherein a bipartite graph includes one or more edges with corresponding weights between each of the first categories and each of the second categories,
   for each bipartite graph:
   a natural language processor in a server utilizing machine learning algorithms is configured to:
   determining a set of edges from the one or more edges based on a weight associated with each of the one or more edges, and
   determining a matching score based on at least a count of edges in the set of edges and a weight associated with each of the set of edges;
   predicting the health condition of the first patient based on at least the matching score associated with each of the one or more bipartite graphs; and
   transmitting a notification message in real-time over the communication network that is indicative of the predicted health condition of the first patient.

2. The method of claim 1 further comprising converting one or more handwritten medical records of the first patient to the one or more first electronic medical records, wherein the one or more handwritten medical records include at least one or more headings and corresponding one or more phrases.

3. The method of claim 2, wherein the one or more phrases correspond to a documentation of one or more health-related observations of the first patient by one or more medical attenders of a medical center.

4. The method of claim 2, further comprising extracting the information to produce the first set of datasets based on the one or more headings and one or more words in the one or more phrases of the one or more headings.

5. The method of claim 1, wherein the weight corresponding to each of the one or more edges in the bipartite graph is determined by use of at least a Jaccard distance metric technique.

6. The method of claim 1 further comprising determining a distance metric based on the matching score associated with each of the one or more bipartite graphs.

7. The method of claim 6 further comprising clustering the first set of datasets into one of one or more predefined groupings based on the determined distance metric and one or more clustering algorithms, wherein the one or more clustering algorithms include at least one of: K-Means, K-Medoids, PAM clustering, model based algorithms like EM for Gaussian Mixture Models, and density based algorithms like DBSCAN.

8. The method of claim 7, wherein the notification message is transmitted to the computing device over the communication network based on the clustered first set of datasets.

9. A system for processing electronic medical records for predicting a health condition of a patient, the system comprising:
a document processor in a server configured to extract information from one or more first electronic medical records of a first patient to produce a first set of datasets,
the one or more first electronic records being received from a computing device over a communication network, and
the first set of datasets including one or more first categories and one or more objects within each first category;
a processor in the server configured to extract one or more second sets of datasets of one or more second patients from a database server based on at least the first set of datasets of the first patient,
the one or more second set of datasets each including one or more second categories and one or more second objects within each second category; and
a graphical processor in the server configured to generate one or more bipartite graphs based on the first set of datasets and the one or more second sets of datasets, wherein a bipartite graph includes one or more edges with corresponding weights between each of the first categories and each of the second categories,
for each bipartite graph:
a natural language processor in a server utilizing machine learning algorithms configured to:
determine a set of edges from the one or more edges based on a weight associated with each of the one or more edges,
determine a matching score based on at least a count of edges in the set of edges and a weight associated with each of the set of edges, and
predict the health condition of the first patient based on at least the matching score associated with each of the one or more bipartite graphs,
wherein the graphical processor transmits a notification message in real-time over the communication network that is indicative of the predicted health condition of the first patient.

10. The system of claim 9, wherein the one or more electronic medical records are obtained by converting, by a multi-function device coupled with at least the computing device, one or more handwritten medical records of the first patient, wherein the one or more handwritten medical records include at least one or more headings and corresponding one or more phrases.

11. The system of claim 10, wherein the one or more phrases correspond to a documentation of one or more health-related observations of the first patient by one or more medical attenders of a medical center.

12. The system of claim 10, wherein the document processor is further configured to determine the first set of datasets based on the one or more headings and one or more words in the one or more phrases of the one or more headings.

13. The system of claim 9, wherein the weight corresponding to each of the one or more edges in the bipartite graph is determined by use of at least a Jaccard distance metric technique.

14. The system of claim 9, wherein the language processor is further configured to determine a distance metric based on the matching score associated with each of the one or more bipartite graphs.

15. The system of claim 14, wherein the natural language processor is further configured to cluster the first set of datasets into one of one or more predefined groupings based on the determined distance metric and one or more clustering algorithms, wherein the one or more clustering algorithms include at least one of: K-Means, K-Medoids, PAM clustering, model based algorithms like EM for Gaussian Mixture Models, and density based algorithms like DBSCAN.

16. The system of claim 15, wherein the notification message is transmitted to the computing device over the communication network based on the clustered first set of datasets.

17. A computer program product for use with a computer, the computer program product comprising a non-transitory computer readable medium, wherein the non-transitory computer readable medium stores a computer program code for processing electronic medical records for predicting a health condition of a patient, wherein the computer program code is executable by:
a document processor in a server is configured to extract information from one or more first electronic medical records of a first patient to produce a first set of datasets,
the one or more first electronic medical records being received from a computing device over a communication network, and
the first set of datasets including one or more first categories and one or more first objects within each first category;
a processor in the server is configured to extract one or more second sets of datasets of one or more second patients from a database server based on at least the first set of datasets of the first patient,
the one or more second set of datasets including one or more second categories and one or more second objects within each second category; and
a graphical processor in the server is configured to generate one or more bipartite graphs based on the first set of datasets and the one or more second sets of datasets, wherein a bipartite graph includes one or more edges with corresponding weights between each of the first categories and each of the second categories,
for each bipartite graph:
a natural language processor in a server utilizing machine learning algorithms is configured to:

determine a set of edges from the one or more edges based on a weight associated with each of the one or more edges, determine a matching score based on at least a count of edges in the set of edges and a weight associated with each of the set of edges, and predict the health condition of the first patient based on at least the matching score associated with each of the one or more bipartite graphs, wherein the graphical processor transmits a notification message in real-time over the communication network that is indicative of the predicted health condition of the first patient.

18. The method of claim 1, further comprising transmitting the one or more first electronic medical records from a requestor-computing device.

19. The method of claim 1, further comprising training a processor to extract the information to produce the first set of datasets.

20. The method of claim 19, further comprising using the one or more generated bipartite graphs to train the processor.

\* \* \* \* \*